United States Patent [19]

Andersson

[11] Patent Number: 4,617,718
[45] Date of Patent: Oct. 21, 1986

[54] METHOD IN THE MANUFACTURE OF TARTAR REMOVING DENTAL INSTRUMENTS

[75] Inventor: Eilert Andersson, Vikmanshyttan, Sweden

[73] Assignee: Dentalvarutjanst AB, Orebro, Sweden

[21] Appl. No.: 638,368

[22] Filed: Aug. 7, 1984

[30] Foreign Application Priority Data

Aug. 16, 1983 [SE] Sweden ................................ 8304420

[51] Int. Cl.$^4$ ...................... B23P 13/04; A61C 17/00
[52] U.S. Cl. ...................................... 29/558; 433/143
[58] Field of Search ........................... 29/558; 51/285; 433/143

[56] References Cited

U.S. PATENT DOCUMENTS 2,511,449 6/1950 Springman .
3,494,081 2/1970 Taylor et al. ........................ 52/285
4,135,528 1/1979 Stark .
4,271,854 6/1981 Bengtsson ............................ 132/89
4,283,174 8/1981 Sertich ................................ 433/119
4,377,381 3/1983 Westmann ........................... 433/143

FOREIGN PATENT DOCUMENTS 28529 5/1981 European Pat. Off. .
699376 10/1940 Fed. Rep. of Germany .
2915044 10/1979 Fed. Rep. of Germany .
840347 4/1939 France .
2406423 10/1977 France ................................ 433/143

Primary Examiner—Howard N. Goldberg
Assistant Examiner—Steven Nichols
Attorney, Agent, or Firm—Cushman, Darby & Cushman

[57] ABSTRACT

A method in the manufacture of tartar removing dental instruments of the type comprising a longitudinal tool portion having a triangular cross-section tapering towards the tip, at least two of the three edges along the lateral faces of the tool portion being ground into cutting edges (5, 6). A profiled blank (1) of a substantially constant triangular cross-section is being ground along one of the lateral faces (2) with the removal of stuff (3) increasing towards the tip (4).

11 Claims, 6 Drawing Figures

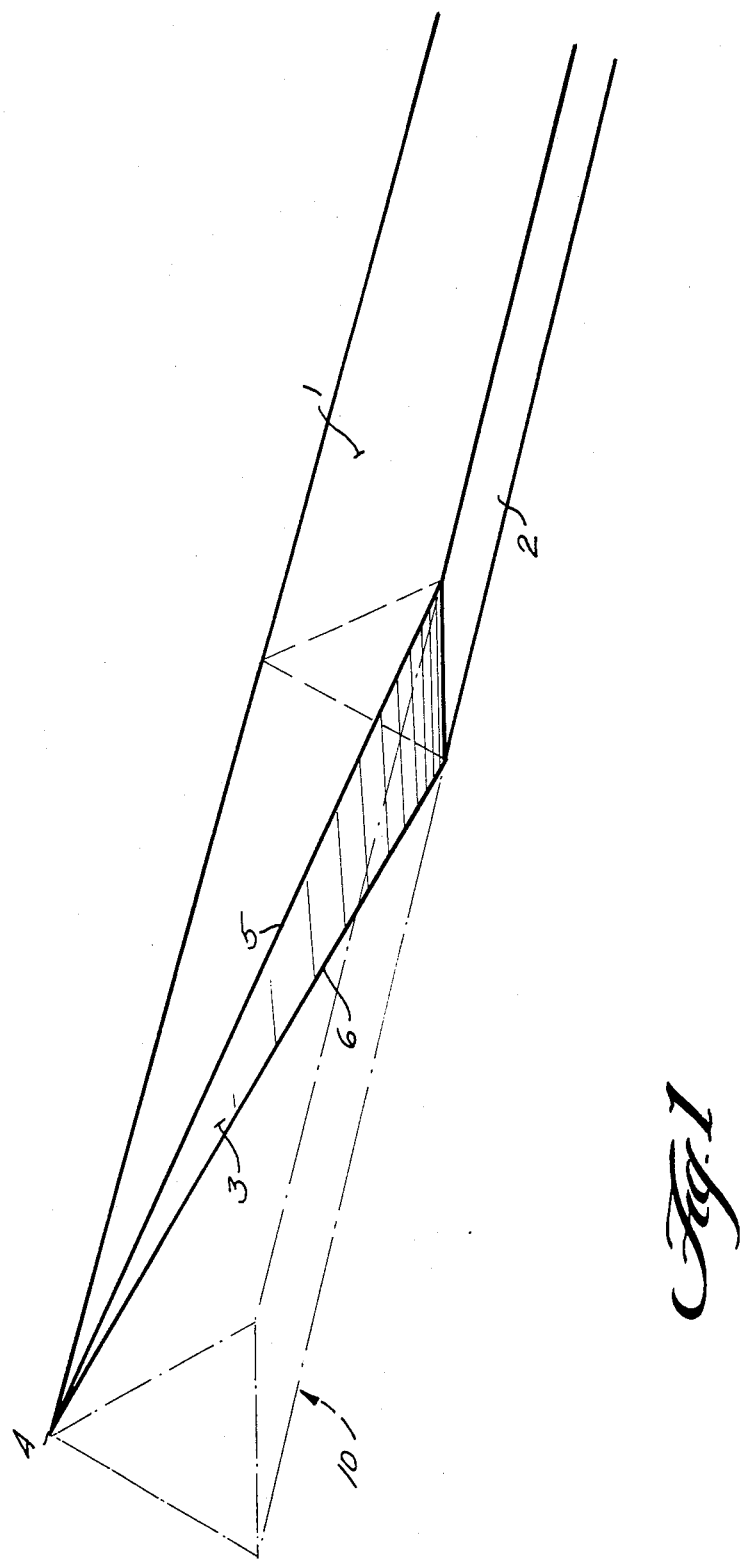

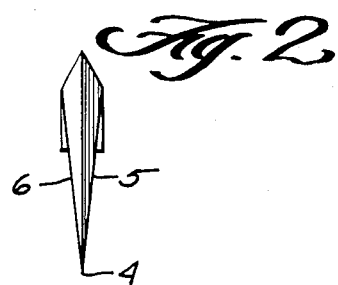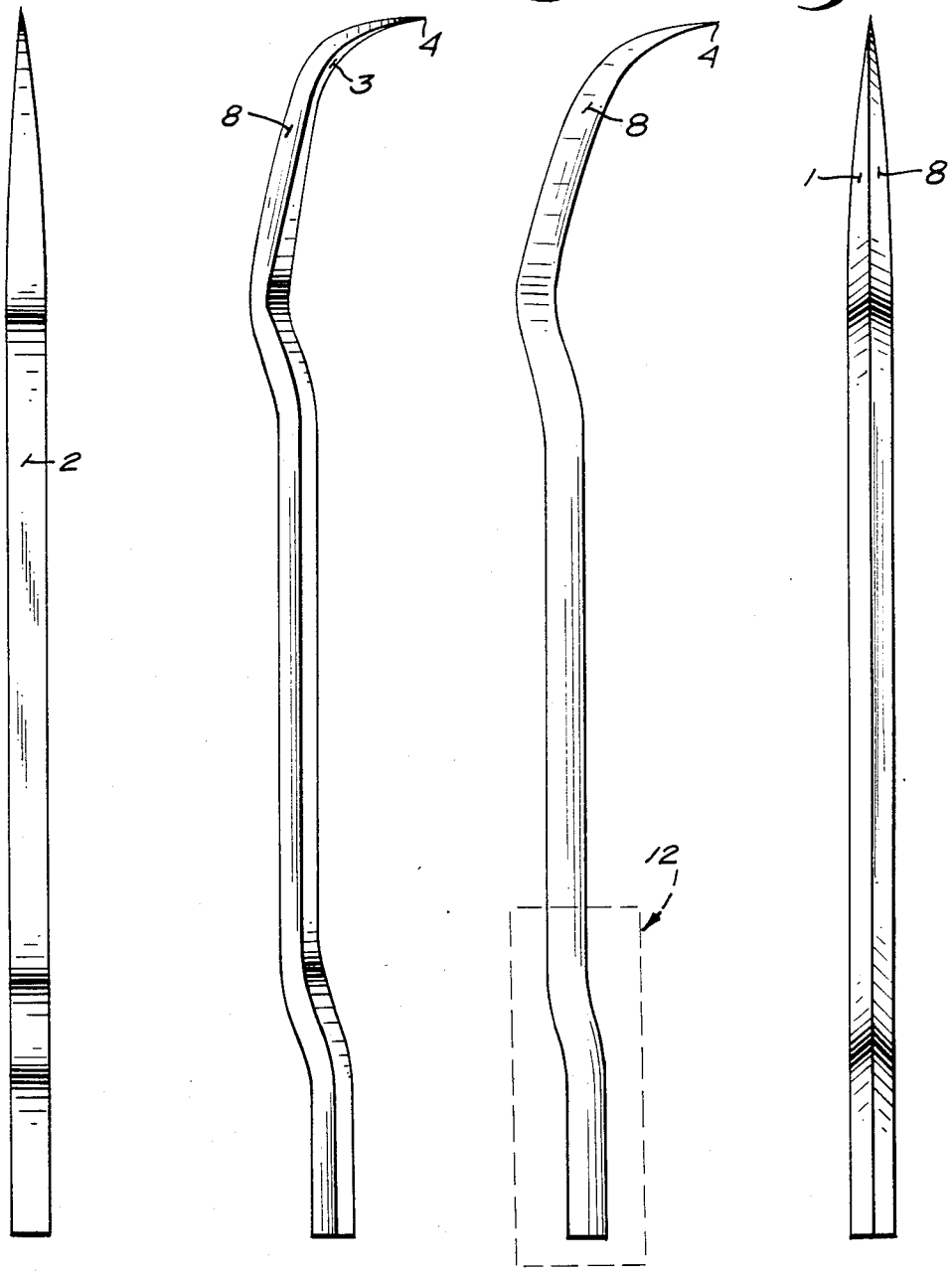

METHOD IN THE MANUFACTURE OF TARTAR REMOVING DENTAL INSTRUMENTS

The present invention relates to a method in the manufacture of tartar removing dental instruments of the kind comprising a longitudinal tool portion having a triangular cross-section tapering towards the tip, at least two of the three edges along the lateral faces of the tool portion being ground into cutting edges. The invention relates particularly to a manufacturing method of said kind, wherein the tip of the tool portion is curved.

In the dentistry nowadays there are used instruments, so-called scalers, for the removal of tartar. The working part of the instrument usually consists of a curved steel profile ground into three facets in such a manner as to terminate in a tip. The two edges along the concave inner side of the tip are used for scraping off tartar, and therefore are ground into sharp cutting edges. In order to obtain good sharpness and make the instrument easy to handle with good accessibility in between the teeth it is also necessary to perform the grinding operation with a correct and uniform angle of the two edges and with an even taper towards the tip. In the manufacture said qualities should be obtained at a low cost and with a reasonable labour input, as a scaler looses its sharpness fairly soon and has to be discarded.

Scalers are commonly manufactured of round steel material ground on three sides in order to obtain the desired triangular final shape. In this known method three grinding operations are required and besides, it is difficult to control the grinding angles at the cutting edges. Particularly when it is desired, as known, to give the instruments its curvature previously to the grinding operation, it is thereafter difficult with full control to grind the two faces situated in the plane of the curvature. Also, on account of the various requirements then involved in the grinding of the several faces, the automatisation of the manufacture has met difficulties.

The main object of the invention is to obviate the above-mentioned problem in connection with the manufacture of tartar removing instruments. Particularly the invention has for its object to simplify and reduce the cost of the manufacture by reducing the number of grinding operations required. A further object is to improve the control of the grinding angles, so that sharp and uniformly shaped cutting edges are had. A still further object is to facilitate the automatisation of the manufacturing process.

Said objects are reached by making use of the characterizing features set forth in the claims.

The manufacture according to the invention starts from a profiled blank having a constant triangular cross-section, which is available in continuous lengths at a low cost. It is possible to restrict the grinding operation to merely one of the faces of the profiled blank, whereby sharpening of the two edges is performed, this being sufficient as the third edge is not used in the operation of the instrument. A further advantage of the triangular cross-section is that the shape of the cross-section remains congruent to that of original blank, independently of how much of the face is being ground off. This involves that the tip of the instrument can be shaped in the same operation as the grinding of the edges, the removal of material simply increasing towards the tip. As a triangular profile easily bends into a concave shape symmetrically to one of the lateral faces, all the above-mentioned problems of obtaining constant angles disappear, as merely the concave face requires grinding and said face is steadily perpendicular to the radius of the curvature. On account of the simplified working the manufacture can be automatized more easily than hitherto.

BRIEF DESCRIPTION OF THE DRAWINGS

FIG. 1 is perspective detailed view of a blank that has been profiled according to the method of the present invention, with material that has been removed shown in dotted line;

FIG. 2 is a top plan view of a completed exemplary dental instrument according to the invention;

FIG. 3 is a front view of the instrument of FIG. 2;

FIG. 4 is a perspective view of the instrument of FIG. 3, turned 45 degrees toward one side;

FIG. 5 is a side view of the instrument of FIG. 3; and

FIG. 6 is a rear view of the instrument of FIG. 3.

DETAILED DESCRIPTION OF THE DRAWINGS

In FIG. 1 the numeral 1 designates one face of a profiled blank of a triangular cross-section, which blank preferably consists of steel and is about 0.5 to 2 mm thick another face of the blank is indicated by reference numeral 8 (see FIGS. 4–6). Over an extension of about 2.5 to 10 mm one of the lateral faces 2 is ground off and forms a substantially flat ground face 3 at an angle to the original face 2, a tip 4 being formed simultaneously as the edges 5 and 6 are sharpened into cutting edges. The material removed as indicated by reference numeral 10, and shown in dotted line, in FIG. 1. The ground face 3 can easily be formed by applying the profiled blank at an angle against a flat grinding face. Subsequent to the grinding operation the tip 4 is bent, and because the asymetrical position of the ground face 3 the point easily bends such that its plane forms a concave face perpendicular to the radius of curvature. FIGS. 2–6 show a finished tool portion which has been worked in said manner, unworked parts of the blank also having been bent in order to improve the accessibility when using the instrument and to facilitate the application of a plastic handle portion upon the back part of the tool portion, which is illustrated diagrammatically by reference numeral 12 in FIG. 5.

The invention is not restricted to the embodiments described and shown, but can be varied within the framework of the following claims.

I claim:

1. A method of manufacturing a tartar removing dental instrument, comprising the steps of:
   (a) selecting a profiled blank having a substantially constant triangular cross-section formed by three lateral faces, each of which are unground and having a first end;
   (b) grinding the blank solely along one of the lateral faces to effect the removal of material, the grinding being practiced to increase the removal of material toward the first end of said one lateral face being ground; and
   (c) continuing grinding to produce an instrument having a triangular cross-section tapering toward a tip formed at the first end, at least two of the three edges along the lateral faces of the instrument adjacent thereto being ground to form cutting edges.

2. A method as recited in claim 1 comprising the further step of curving the tip that has been formed, so that the lateral face which has been ground is concave.

3. A method as recited in claim 2 comprising the further step of bending portions of the blank remote from the tip to facilitate attachment of a handle portion thereto.

4. A method as recited in claim 3 comprising the further step of applying a plastic handle portion to the portion of the blank bent for receipt of the handle portion.

5. A method as recited in claim 4 wherein the profiled blank consists of a steel profiled blank.

6. A method as recited in claim 5 wherein the profiled blank comprises an equilateral triangle in cross-section.

7. A method as recited in claim 1 wherein the profiled blank comprises an equilateral triangle in cross-section.

8. A method as recited in claim 1 comprising the further step of bending portions of the blank remote from the tip to facilitate attachment of a handle portion thereon.

9. A method as recited in claim 8 comprising the further step of applying a plastic handle portion to the portion of the blank bent for receipt of the handle portion.

10. A method as recited in claim 1 wherein the profiled blank consists of a steel profiled blank.

11. A method as recited in claim 10 wherein the profiled blank comprises an equilateral triangle in cross-section.

* * * * *